(12) United States Patent
L'Alloret

(10) Patent No.: US 6,994,846 B2
(45) Date of Patent: Feb. 7, 2006

(54) COMPOSITION FOR COSMETIC OR DERMATOLOGICAL USE CONTAINING A TRIBLOCK POLYMER

(75) Inventor: Florence L'Alloret, Paris (FR)

(73) Assignee: L'Oreal, Paris (FR)

(*) Notice: Subject to any disclaimer, the term of this patent is extended or adjusted under 35 U.S.C. 154(b) by 0 days.

(21) Appl. No.: 10/197,555

(22) Filed: Jul. 18, 2002

(65) Prior Publication Data
US 2003/0059391 A1 Mar. 27, 2003

(30) Foreign Application Priority Data
Jul. 18, 2001 (FR) .................... 01 09614

(51) Int. Cl.
*A61K 7/48* (2006.01)

(52) U.S. Cl. .............. 424/78.18; 424/401; 424/61; 424/701; 424/707

(58) Field of Classification Search ........... 424/401, 424/78.31–78.38, 61, 70.1, 78.18
See application file for complete search history.

(56) References Cited

U.S. PATENT DOCUMENTS 4,505,827 A * 3/1985 Rose et al. ............... 507/228

6,689,856 B2 * 2/2004 L'alloret ................. 526/333

FOREIGN PATENT DOCUMENTS

EP 0 947 527 A 10/1999

OTHER PUBLICATIONS

C. Tsitsilianis et al.: "An Associative Polyelectrolyte End-Capped with Short Polystyrene Chains." Macromolecules, vol. 33, No. 8 2000, pp. 2936-2943, XP002202464.
EP 1002 527 (May 24, 2000) Abstract.
FR 2710646 (Apr. 7, 1995) Abstract.

* cited by examiner

*Primary Examiner*—Jyothsna Venkat
(74) *Attorney, Agent, or Firm*—Oblon, Spivak, McClelland, Maier & Neustadt, P.C.

(57) ABSTRACT

The present patent application relates to a cosmetic and/or dermatological composition comprising at least one aqueous phase including at least one water-soluble or water-dispersible polymer, of triblock structure B-A-B in which A is an ionic water-soluble polymer block and B is a hydrophobic polymer block, the amount of polymer block A being greater than or equal to 50% of the total weight of the triblock polymer.

The invention also relates to the use of the said composition, especially in cosmetics for caring for, cleansing, protecting and/or making up the skin, keratin fibers and/or mucous membranes.

42 Claims, No Drawings

COMPOSITION FOR COSMETIC OR DERMATOLOGICAL USE CONTAINING A TRIBLOCK POLYMER

The present patent application relates to a cosmetic and/or dermatological composition comprising at least one aqueous phase including at least one block polymer, and to uses thereof in cosmetics or dermatology, especially for caring for, cleansing, protecting and/or making up keratin materials (skin, mucous membranes or keratin fibres such as the hair and the eyelashes).

Cosmetic compositions, especially those intended for caring for or cleansing human skin or the hair, usually comprise an aqueous phase that is gelled, i.e. thickened, using one or more thickener(s) or gelling agent(s). These may be, for example, lotions which are aqueous solutions not containing an oily phase, or emulsions which may be direct oil-in-water (O/W) emulsions including a fatty phase or oily phase dispersed in an aqueous continuous phase, or water-in-oil (W/O) reverse emulsions including an aqueous phase dispersed in an oily continuous phase. The term "emulsions" means herein both the dispersions obtained in the absence of emulsifying surfactants and the emulsions obtained in the presence of emulsifying surfactants.

Oil-in-water emulsions are the emulsions most frequently sought in cosmetics due to the fact that, when applied to the skin, they give a softer, less greasy, fresher and lighter feel than water-in-oil emulsion systems, by virtue of the presence of water in the continuous outer phase.

The nature of the compounds used for gelling the aqueous phase and their content in the composition are chosen as a function of the desired type of texture, which may range from fluid lotions to more or less thick emulsions that may constitute milks or creams. The main thickeners or gelling agents used in cosmetics are chosen from the following compounds:

natural polymers such as xanthan gum and guar gum or cellulose derivatives, starches and alginates. These compounds do not provide cosmetic properties that are good enough to be used alone as thickener or gelling agent. Moreover, their natural origin may induce problems of reproducibility between batches of raw material, reflected by a variability in the gelling power;
  crosslinked polymeric gelling agents such as the Carbopols sold by the company Goodrich or crosslinked and at least partially neutralized 2-acrylamido-2-methylpropanesulfonic acid polymers such as, for example, the product sold under the name Hostacerin AMPS by the company Clariant. These crosslinked gelling agents demand that a specific protocol for dispersion in water or in the oily phase be followed in order to obtain reproducible levels of viscosity. Various gelling agents are proposed in order to limit these dispersion problems, such as, for example, the ETD carbopols, which are specific "easy to disperse" carbopols, or alternatively crosslinked gelling agents dispersed in an oil or a mixture of oils, such as the polyacrylamide sold by the company SEPPIC under the name Sépigel 305. However, dispersing the ETD Carbopols in water demands that a specific protocol for swelling the polymer be followed, whereas the gelling agents supplied as a dispersion in an oil necessarily introduce an oily phase and surfactants into the composition.

Moreover, the gelling agents mentioned above do not have amphiphilic properties capable of stabilizing the globules of the dispersed phase in the continuous phase of an emulsion. It is thus necessary either to introduce emulsifying surfactants in order to obtain stable emulsions or to introduce only small amounts of oil (in general less than 10%) and to design highly gelled textures. However, efforts are continually under way to reduce the amount of emulsifying surfactant in emulsions in order to improve their harmlessness with respect to the skin, the eyes and the scalp. Moreover, it is sought to be able to have the greatest possible freedom in the formulation, that is to say to be able to obtain a composition that is stable, irrespective of the amount of oil introduced and irrespective of the final viscosity of the composition (greater or lesser extent of gelation).

Crosslinked amphiphilic gelling agents exist, such as the products sold by the company Goodrich under the name Pemulen, which allow larger oil fractions to be incorporated, but they are generally used in the presence of other hydrophilic gelling agents since their gelling and cosmetic properties are not large and/or good.

There is thus still a need for a compound for gelling an aqueous phase in order to obtain a broad range of textures, and having good cosmetic properties, which is easy to disperse in water and whose thickening/gelling power is reproducible, and which preferably, moreover, has both gelling and emulsifying properties.

The Applicant has discovered, unexpectedly, a novel family of block polymers that allow the aim of the invention to be achieved. These block polymers are water-soluble or water-dispersible polymers of triblock structure B-A-B, in which A is an ionic water-soluble polymer block and B is a hydrophobic polymer block; they have aqueous-phase-gelling properties, at weight concentrations of less than 15% by weight. These, polymers make it possible to obtain a wide range of textures with good cosmetic properties. These polymers are easy to dissolve or disperse in water and the gelling properties obtained are reproducible from one batch to another.

These polymers also make it possible to prepare cosmetic or dermatological compositions including an aqueous phase, the pH of which may vary within a wide range and the viscosity of which remains stable over time at room temperature or at higher temperatures. They also make it possible to prepare homogenic, non-flowing, non-runny products that are soft and slippery when applied and stable on storage.

The present invention relates to a cosmetic and/or dermatological composition, characterized in that it comprises at least one aqueous phase including at least one water-soluble or water-dispersible polymer, of triblock structure B-A-B in which A is an ionic water-soluble polymer block and B is a hydrophobic polymer block, the amount of polymer block A being greater than or equal to 50% of the total weight of the triblock polymer.

The proportion of at least 50% of polymer block A makes it possible to obtain good gelling properties of the polymer.

In addition, according to one preferred embodiment of the invention, the triblock polymers used according to the invention as gelling agents contain an ionic water-soluble polymer block A that is totally water-soluble, i.e. that is completely free of hydrophobic monomer, and hydrophobic polymer blocks B that are totally hydrophobic, i.e. that are completely free of hydrophilic monomer.

The preferred triblock polymers, B-A-B, comprising a totally water-soluble ionic polymer block A and totally hydrophobic polymer blocks B, have the advantage of being easy to synthesize and of giving gelation that is as good as the others for lower concentrations.

Thus, the composition according to the invention preferably comprises at least one aqueous phase comprising at least one water-soluble or water-dispersible polymer, of triblock structure B-A-B in which A is a totally water-soluble ionic polymer block and B is a totally hydrophobic polymer block, and in which the amount of polymer block A is greater than or equal to 50% of the total weight of the triblock polymer.

The triblock polymers used according to the invention, and especially the preferred polymers comprising a totally water-soluble ionic polymer block A and two totally hydrophobic polymer blocks B, make it possible to obtain satisfactory gelation of the aqueous phases of the compositions for topical application, especially cosmetic or dermatological compositions.

A subject of the invention is also the use of at least one water-soluble or water-dispersible polymer, of triblock structure B-A-B, in which A is an ionic water-soluble polymer block and B is a hydrophobic polymer block, and in which the amount of polymer block A is greater than or equal to 50% of the total weight of the triblock polymer, to gel and/or thicken a cosmetic and/or dermatological composition comprising at least one aqueous phase.

Preferably, a subject of the invention is also the use of at least one water-soluble or water-dispersible polymer, of triblock structure B-A-B, in which A is a totally water-soluble ionic polymer block and B is a totally hydrophobic polymer block, and in which the amount of polymer block A is greater than or equal to 50% of the total weight of the triblock polymer, to gel a cosmetic or dermatological composition comprising at least one aqueous phase.

As described above, the triblock polymers used according to the invention make it possible to obtain good gelation of the aqueous phases. Moreover, this gelling power has the advantage of changing relatively little in the presence of surfactants, whether they are nonionic or ionic (anionic or cationic) and whether they are emulsifying surfactants or detergent surfactants (or foaming surfactants). When the amount of surfactant is high (greater than 1%), the gelling power remains, although it may be reduced.

Moreover, the Applicant has found, unexpectedly, that the polymers of the invention of triblock structure B-A-B, in which A is an ionic water-soluble polymer block and B is a hydrophobic polymer block, the amount of polymer block A being greater than or equal to 50% of the total weight of the triblock polymer, have the emulsifying properties and may also be used for preparing emulsifying surfactant-free emulsions or emulsions containing small amounts of emulsifying surfactant (from 0 to about 1% by weight with respect to the total weight of the composition, and preferably less than 0.5% by weight), in particular of O/W emulsions. In the present application, the expression "emulsifying surfactants" means monomeric surfactants having emulsifying properties.

Thus, another subject of the invention is a cosmetic and/or dermatological composition in the form of an oil-in-water emulsion comprising an oily phase dispersed in an aqueous phase, characterized in that it comprises from 0 to about 1% by weight of emulsifying surfactant relative to the total weight of the composition, and in that it is in accordance with the composition defined above comprising a water-soluble or water-dispersible polymer, of triblock structure B-A-B, in which A is an ionic water-soluble polymer block and B is a hydrophobic polymer block, and in which the amount of polymer block A is greater than or equal to 50% of the total weight of the triblock polymer. The emulsion thus obtained is considered as an emulsion that is free of emulsifying surfactant.

Moreover, the Applicant has also found, unexpectedly, that synergistic gelation occurs when use is made of a water-soluble or water-dispersible polymer, of triblock structure B-A-B in which A is an ionic water-soluble polymer block and B is a hydrophobic polymer block, the amount of polymer block A being greater than or equal to 50% of the total weight of the triblock polymer, with a water-soluble or water-dispersible neutral diblock polymer A'-B in which A' is a neutral water-soluble polymer block and B is a hydrophobic polymer block.

Thus, a subject of the invention is also a cosmetic and/or dermatological composition, characterized in that it comprises at least one aqueous phase comprising at least one water-soluble or water-dispersible polymer, of triblock structure B-A-B in which A is an ionic water-soluble polymer block and B is a hydrophobic polymer block, and in which the amount of polymer block A is greater than or equal to 50% of the total weight of the triblock polymer, and at least one water-soluble or water-dispersible neutral diblock polymer A'-B in which A' is a neutral water-soluble polymer block and B is a hydrophobic polymer block.

In the present patent application, the expression "water-soluble or water-dispersible" means polymers which, when introduced into an aqueous phase at 25° C., at a weight concentration equal to 1%, allow the production of a macroscopically homogeneous and transparent solution, i.e. a solution with a maximum light transmittance value, at a wavelength equal to 500 nm, through a sample 1 cm thick, of at least 70% and preferably of at least 80%.

In the present patent application, the expression "polymer block" means a polymer (homopolymer or copolymer) whose molar mass is greater than 400 g/mol and preferably greater than 800 g/mol.

In the present patent application, the expression "hydrophobic block" means a polymer (homopolymer or copolymer) which, when introduced into a hydrocarbon solvent at 25° C., at a weight concentration equal to 1%, allows the production of a macroscopically homogeneous and transparent solution, i.e. a solution with a maximum light transmittance value, at a wavelength equal to 500 nm, through a sample 1 cm thick, of at least 70% and preferably of at least 80%. The hydrocarbon solvent used herein has a dielectric constant, measured at 25° C., of less than 50; this solvent may be chosen especially from alkanes such as cyclohexane (dielectric constant: 2.02); aromatic solvents such as ethylbenzene (dielectric constant: 2.4); ketones such as cyclohexanone (dielectric constant: 18.3); ethers such as diethyl ether (dielectric constant=4.4); alcohols such as cyclohexanol (dielectric constant: 15.0); chlorohydrocarbon solvents such as dichloromethane (dielectric constant: 9.08); amides such as dimethyl-formamide; and esters such as ethylacetate (dielectric constant: 6.02).

Since the compositions of the invention are intended for topical application, they contain a physiologically acceptable medium, i.e. a medium that is compatible with all keratin materials such as the skin, the nails, mucous membranes and the hair or any other area of body skin.

In the water-soluble or water-dispersible polymers of triblock structure B-A-B, used in the composition of the invention, the ionic water-soluble block A is obtained from one or more water-soluble monomers (Ia) or salts thereof, such as, for example:

(meth)acrylic acid,
styrenesulfonic acid,
vinylsulfonic acid and (meth)allylsulfonic acid,
vinylphosphonic acid, maleic acid,
itaconic acid,
crotonic acid,
methyldiallylammonium chloride,
dimethylvinylimidazolium chloride,
ethylenic carboxybetaines or sulfobetaines obtained, for example, by quaternization of ethylenically unsaturated monomers including an amine function, with sodium salts of carboxylic acids containing a labile halogen (e.g.: chloroacetate) or with cyclic sulfones (e.g.: propanesulfone),
water-soluble vinyl monomers of formula (I) below:

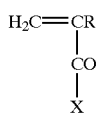
(I)

in which:
R is chosen from H, —$CH_3$, —$C_2H_5$ and —$C_3H_7$;
X is chosen from:
alkyloxides of the type —$OR_1$ in which $R_1$ is a linear or branched, saturated or unsaturated hydrocarbon radical containing from 1 to 6 carbon atoms, substituted with at least one carboxylate ($CO_2^-$) and/or sulfonic (—$SO_3^-$) and/or sulfate (—$SO_4^-$) and/or phosphate (—$PO_4H_2^-$) and/or quaternary ammonium (—$N^+R_2R_3R_4$) group, the radicals $R_2$, $R_3$ and $R_4$ being, independently of each other, a linear or branched, saturated or unsaturated hydrocarbon radical containing 1 to 6 carbon atoms, with the proviso that the sum of the carbon atoms of $R_1+R_2+R_3+R_4$ does not exceed 6. In addition, the radical $R_1$ may optionally be substituted with a halogen atom (iodine, bromine, chlorine or fluorine); a hydroxyl (—OH); carboxylic acid (—COOH); ether (—O—); primary amine (—$NH_2$); secondary amine (—$NHR_5$); tertiary amine (—$NR_5R_6$) group, the radicals $R_5$ and $R_6$ being, independently of each other, a linear or branched, saturated or unsaturated hydrocarbon radical containing 1 to 6 carbon atoms, with the proviso that the sum of the carbon atoms of $R_1+R_5+R_6$ does not exceed 6.

An example of vinyl monomers including ester groups (X=$OR_1$) that may be mentioned is quaternized dimethylaminoethyl methacrylate (DMAEMA).
groups —$NH_2$, —$NHR_7$ and —$NR_7R_8$ in which $R_7$ and $R_8$ are, independently of each other, a linear or branched, saturated or unsaturated hydrocarbon radical containing 1 to 6 carbon atoms, with the proviso that the total number of carbon atoms of $R_7+R_8$ does not exceed 6, the said radicals $R_7$ and/or $R_8$ being substituted with at least one carboxylate ($CO_2^-$) and/or sulfonic (—$SO_3^-$) and/or sulfate (—$SO_4^-$) and/or phosphate (—$PO_4H_2^-$) and/or quaternary amine (—$N^+R_9R_{10}R_{11}$) group, the radicals $R_9$, $R_{10}$ and $R_{11}$ being, independently of each other, a linear or branched, saturated or unsaturated hydrocarbon radical containing 1 to 6 carbon atoms, with the proviso that the sum of the carbon atoms of $R_7+R_8+R_9+R_{10}+R_{11}$ does not exceed 6. In addition, the radicals $R_7$ and/or $R_8$ may optionally be substituted with a halogen atom (iodine, bromine, chlorine or fluorine); a hydroxyl (—OH); carboxylic acid (COOH), ether (—O—); primary amine (—$NH_2$); secondary amine (—$NHR_5$); or tertiary amine (—$NR_5R_6$) group, in which $R_5$ and $R_6$ have the meanings given above, with the proviso that the sum of the carbon atoms of $R_7+R_8+R_5+R_6$ does not exceed 6.

Examples of vinyl monomers including amide groups that may be mentioned are 2-acrylamido-2-methyl-propanesulfonic acid (AMPS) and (meth)acrylamido-propyltrimethylammonium chloride (APTAC and MAPTAC);
the substituents R and X being such that the monomer of formula (I) is water-soluble;
and mixtures of these monomers (Ia).

Along with the water-soluble monomers (Ia) mentioned above and always present, the ionic water-soluble block A of the polymers of the invention may optionally comprise one or more monomers chosen from hydrophobic monomers (Ib), neutral water-soluble monomers (Ic) and mixtures thereof. The hydrophobic monomers optionally present should be in an amount that is low enough for the block A to be water-soluble.

As examples of hydrophobic monomers (Ib) that may be used in the ionic water-soluble block A, mention may be made of:
styrene and its derivatives such as 4-butyl-styrene, α-methylstyrene and vinyltoluene;
vinyl acetate of formula $CH_2$=CH—$OCOCH_3$;
vinyl ethers of formula $CH_2$=$CHOR_{12}$ in which $R_{12}$ is a linear or branched, saturated or unsaturated hydrocarbon radical containing from 1 to 6 carbon atoms;
acrylonitrile;
caprolactone;
vinyl chloride and vinylidene chloride;
unsaturated silicone monomers such as methacryl-oxypropyltris(trimethylsiloxy)silane and silicone methacrylamides,
hydrophobic vinyl monomers of formula (II) below:

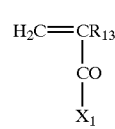
(II)

in which:
$R_{13}$ is chosen from H, —$CH_3$, —$C_2H_5$ and —$C_3H_7$;
$X_1$ is chosen from:
alkyloxides of the type —$OR_{14}$ in which $R_{14}$ is a linear or branched, saturated or unsaturated hydrocarbon radical containing from 1 to 6 carbon atoms. Examples of monomers of this type that may be mentioned are methyl methacrylate, ethyl methacrylate, n-butyl (meth)acrylate, tert-butyl (meth)acrylate, cyclohexyl acrylate, isobornyl acrylate and 2-ethylhexyl acrylate.
groups —$NH_2$, —$NHR_{15}$ and —$NR_{15}R_{16}$ in which $R_{15}$ and $R_{16}$ are, independently of each other, linear or branched, saturated or unsaturated hydrocarbon radicals containing 1 to 6 carbon atoms, with the proviso that the total number of carbon atoms of $R_{15}+R_{16}$ does not exceed 6.
the substituents $R_{13}$ and $X_1$ being such that the monomer of formula (II) is hydrophobic.
and mixtures of these monomers.
Examples of neutral water-soluble monomers (Ic) that may be mentioned include:

(meth)acrylamide,
N-vinylacetamide and N-methyl-N-vinylacetamide,
N-vinylformamide and N-methyl-N-vinylformamide,
maleic anhydride,
vinylamine,
N-vinyllactams including a cyclic alkyl group containing from 4 to 9 carbon atoms, such as N-vinyl-pyrrolidone, N-butyrolactam and N-vinylcaprolactam,
vinyl alcohol of formula $CH_2=CHOH$,
water-soluble vinyl monomers of formula (III) below:

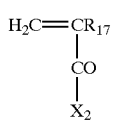

(III)

in which:
R$_{17}$ is chosen from H, —CH$_3$, —C$_2$H$_5$ and —C$_3$H$_7$;
X$_2$ is chosen from:
alkyloxides of the type —OR$_{18}$ in which R$_{18}$ is a linear or branched, saturated or unsaturated hydrocarbon radical containing from 1 to 6 carbon atoms, optionally substituted with a halogen atom (iodine, bromine, chlorine or fluorine); a carboxylic acid (—COOH), hydroxyl (—OH); ether (—O—); primary amine (—NH$_2$) ; secondary amine (—NHR$_{19}$) or tertiary amine (—NR$_{19}$R$_{20}$) group, the radicals R$_{19}$ and R$_{20}$ being, independently of each other, a linear or branched, saturated or unsaturated hydrocarbon radical containing 1 to 6 carbon atoms, with the proviso that the sum of the carbon atoms of R$_{18}$+R$_{19}$+R$_{20}$ does not exceed 6. Examples of monomers of formula (III) in which X$_2$ is a radical —OR$_{18}$ that may be mentioned include glycidyl (meth)acrylate, hydroxyethyl methacrylate and ethylene glycol (meth)acrylate, diethylene glycol (meth)acrylate and polyalkylene glycol (meth)acrylates.
groups —NH$_2$, —NHR$_{21}$ and —NR$_{21}$R$_{22}$ in which R$_{21}$ and R$_{22}$ are, independently of each other, linear or branched, saturated or unsaturated hydrocarbon radicals containing 1 to 6 carbon atoms, with the proviso that the total number of carbon atoms of R$_{21}$+R$_{22}$ does not exceed 6, the said radicals R$_{21}$ and R$_{22}$ optionally being substituted with a halogen atom (iodine, bromine, chlorine or fluorine); a hydroxyl (—OH); carboxylic acid (CO$_2$H); ether (—O—); primary amine (—NH$_2$); secondary amine (—NHR$_{23}$); or tertiary amine (—NR$_{23}$R$_{24}$) group, the radicals R$_{23}$ and R$_{24}$ being, independently of each other, a linear or branched, saturated or unsaturated hydrocarbon radical containing 1 to 6 carbon atoms, with the proviso that the sum of the carbon atoms of R$_{21}$+R$_{22}$+R$_{23}$+R$_{24}$ does not exceed 6. Examples of monomers of this type that may be mentioned include dimethylaminoethylmethacrylamide and N,N-dimethylacrylamide.
the substituents R$_{17}$ and X$_2$ being such that the monomer of formula (III) is water-soluble.
mixtures of these monomers (Ic).
In addition to the water-soluble monomers mentioned above, the ionic water-soluble block A may also be an ionic water-soluble polymer such as, for example, polyethyleneimine.
The ionic water-soluble block A is totally or partially neutralized. The expression "partially neutralized" means a neutralization of at least 20 mol %. The degree of neutralization is preferably at least 30% and better still from 40 to 100 mol %. The ionic water-soluble block A may be neutralized with a mineral or organic base. This base may be chosen, for example, from sodium, ammonium, lithium, calcium or magnesium salts, ammonium salts substituted with 1 to 4 alkyl groups bearing from 1 to 15 carbon atoms, or from organic bases such as monoethanolamine, diethanolamine, triethanolamine, aminoethylpropanediol or N-methylglucamine, and basic amino acids, such as arginine and lysine, and mixtures thereof.
The hydrophobic block B is obtained from one or more hydrophobic monomers (Id) such as, for example:
styrene and its derivatives such as 4-butyl-styrene, α-methylstyrene and vinyltoluene,
vinyl acetate of formula $CH_2=CH-OCOCH_3$,
vinyl ethers of formula $CH_2=CHOR_{25}$ in which R$_{25}$ is a linear or branched, saturated or unsaturated hydrocarbon radical containing from 1 to 22 carbon atoms,
acrylonitrile,
vinyl chloride and vinylidene chloride,
caprolactone,
alkenes such as ethylene, propylene, butylene and butadiene,
unsaturated silicone monomers such as methacryl-oxypropyltris(trimethylsiloxy)silane and silicone methacrylamides, and also silicone derivatives leading, after polymerization, to silicone polymers such as polydimethylsiloxane,
hydrophobic vinyl monomers of formula (IV) below:

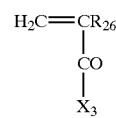

(IV)

in which:
R$_{26}$ is chosen from H, —CH$_3$, —C$_2$H$_5$ or —C$_3$H$_7$;
X$_3$ is chosen from:
alkyloxides of the type —OR$_{27}$ in which R$_{27}$ is a linear or branched, saturated or unsaturated hydrocarbon radical containing from 1 to 22 carbon atoms, optionally substituted with a halogen atom (iodine, bromine, chlorine or fluorine); a carboxylate (—CO$_2$$^-$), sulfonic (—SO$_3$$^-$), sulfate (—SO$_4$$^-$), phosphate (—PO$_4$H$_2$$^-$), hydroxyl (—OH), carboxylic acid (—COOH), ether (—O—), primary amine (—NH$_2$), secondary amine (—NHR$_{28}$), tertiary amine (—NR$_{28}$R$_{29}$) or quaternary ammonium (—N$^+$R$_{28}$R$_{29}$R$_{30}$) group, the radicals R$_{28}$, R$_{29}$ and R$_{30}$ being, independently of each other, a linear or branched, saturated or unsaturated hydrocarbon radical containing 1 to 22 carbon atoms, with the proviso that the sum of the carbon atoms of R$_{27}$+R$_{28}$+R$_{29}$+R$_{30}$ does not exceed 22; or R$_{27}$ is a perfluoroalkyl radical preferably containing from 1 to 18 carbon atoms.
As examples of hydrophobic vinyl monomers including alkyl oxide groups of the type —OR$_{27}$, mention may be made of methyl methacrylate, ethyl methacrylate, n-butyl (meth)acrylate, tert-butyl (meth)acrylate, cyclohexyl acrylate, isobornyl acrylate and 2-ethylhexyl acrylate. Examples of monomers of formula (IV) with a perfluoroalkyl radical constituting the group $R_{27}$ that may be mentioned include ethylperfluorooctyl acrylate and trifluoromethyl (meth)acrylate;

groups —$NH_2$, —$NHR_{31}$ and —$NR_{31}R_{32}$ in which the radicals $R_{31}$, and $R_{32}$ are, independently of each other, a linear or branched, saturated or unsaturated hydrocarbon radical containing 1 to 22 carbon atoms, with the proviso that the total number of carbon atoms of $R_{31}+R_{32}$ does not exceed 22, the said radicals $R_{31}$ and $R_{32}$ optionally being substituted with a halogen atom (iodine, bromine, chlorine or fluorine); a hydroxyl (—OH), ether (—O—), carboxylate (—$CO_2^-$), sulfonic (—$SO_3^-$), sulfate (—$SO_4^-$), phosphate (—$PO_4H_2^-$), carboxylic acid (—COOH), primary amine (—$NH_2$), secondary amine (—$NHR_{28}$), tertiary amine (—$NR_{28}R_{29}$) or quaternary ammonium (—$N^+R_{28}R_{29}R_{30}$) group, in which $R_{28}$, $R_{29}$ and $R_{30}$ have the same meanings as those given above, with the proviso that the sum of the carbon atoms of $R_{31}+R_{32}+R_{28}+R_{29}+R_{30}$ does not exceed 22. $R_{31}$ and $R_{32}$, independently of each other, may also be a perfluoroalkyl radical preferably containing from 1 to 18 carbon atoms.

the substituents $R_{26}$ and $X_3$ being such that the monomer of formula (IV) is hydrophobic;

and mixtures of these monomers (Id).

Along with the hydrophobic monomers (Id) mentioned above and always present, the hydrophobic block B of the polymers of the invention may optionally be obtained from one or more ionic or neutral water-soluble monomers (Ie), the said water-soluble monomers being present in an amount that is low enough for the block B to be hydrophobic.

Examples of water-soluble monomers (Ie) that may be mentioned include the following compounds, or salts thereof:

(meth)acrylic acid;
styrenesulfonic acid;
vinylsulfonic acid and (meth)allylsulfonic acid;
vinylphosphonic acid;
maleic anhydride;
maleic acid;
itaconic acid;
crotonic acid;
dimethyldiallylammonium chloride;
methylvinylimidazolium chloride;
(meth)acrylamide;
N-vinylacetamide and N-methyl-N-vinylacetamide;
N-vinylformamide and N-methyl-N-vinylformamide;
N-vinyllactams including a cyclic alkyl group containing from 4 to 9 carbon atoms, such as N-vinyl-pyrrolidone, N-butyrolactam and N-vinylcaprolactam,
vinyl alcohol of formula $CH_2$=CHOH;
2-vinylpyridine and 4-vinylpyridine;
the water-soluble vinyl monomers of formula (V) below:

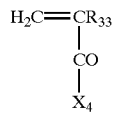

(V)

in which:
$R_{33}$ is chosen from H, —$CH_3$, —$C_2H_5$ and —$C_3H_7$;
$X_4$ is chosen from:

alkyloxides of the type —$OR_{34}$ in which $R_{34}$ is a linear or branched, saturated or unsaturated hydrocarbon radical containing from 1 to 6 carbon atoms, optionally substituted with a halogen atom (iodine, bromine, chlorine or fluorine); a carboxylate (—$COO^-$), carboxylic acid (—COOH), sulfonic (—$SO_3^-$), sulfate (—$SO_4^-$), phosphate (—$PO_4H_2^-$), hydroxyl (—OH), ether (—O—), primary amine (—$NH_2$), secondary amine (—$NHR_{35}$), tertiary amine (—$NR_{35}R_{36}$) or a quaternary ammonium (—$N^+R_{35}R_{36}R_{37}$) group, the radicals $R_{35}$, $R_{36}$ and $R_{37}$ being, independently of each other, a linear or branched, saturated or unsaturated hydrocarbon radical containing 1 to 6 carbon atoms, with the proviso that the sum of the carbon atoms of $R_{34}+R_{35}+R_{36}+R_{37}$ does not exceed 6.

Examples of vinyl monomers including ester groups ($X_4$=$OR_{34}$) that may be mentioned include quaternized dimethylaminoethyl methacrylate (DMAEMA), glycidyl (meth)acrylate, hydroxyethyl methacrylate and ethylene glycol (meth)acrylate, diethylene glycol (meth)acrylate or polyalkylene glycol (meth)acrylates.

groups —$NH_2$, —$NHR_{38}$ and —$NR_{38}R_{39}$ in which the radicals $R_{38}$ and $R_{39}$ are, independently of each other, linear or branched, saturated or unsaturated hydrocarbon radicals containing 1 to 6 carbon atoms, with the proviso that the total number of carbon atoms of $R_{38}+R_{39}$ does not exceed 6, the said radicals $R_{38}$ and/or $R_{39}$ optionally being substituted with a halogen atom (iodine, bromine, chlorine or fluorine); a carboxylate (—$COO^-$), sulfonic (—$SO_3^-$); sulfate ($SO_4^-$); phosphate (—$PO_4H_2^-$); hydroxyl (—OH); carboxylic acid (—COOH); ether (—O—); primary amine (—$NH_2$); secondary amine (—$NHR_{35}$); tertiary amine (—$NR_{35}R_{36}$) or a quaternary ammonium (—$N^+R_{35}R_{36}R_{37}$) group, in which $R_{35}$, $R_{36}$ and $R_{37}$ have the same meaning as mentioned above, with the proviso that the sum of the carbon atoms of $R_{38}+R_{39}+R_{35}+R_{36}+R_{37}$ does not exceed 6.

Examples of water-soluble vinyl monomers of formula (V) including amide groups that may be mentioned are 2-acrylamido-2-methylpropanesulfonic acid (AMPS), (meth)acrylamidopropyltrimethylammonium chloride (APTAC and MAPTAC) and N,N-dimethylacrylamide.

the substituents $R_{33}$ and $X_4$ being such that the monomer of formula (V) is water-soluble.

and mixtures of the monomers (Ie).

In the triblock polymer B-A-B, the two blocks B may be identical or different.

The triblock polymers used in the composition of the invention have a molar mass ranging from 1000 g/mol to 500 000 g/mol and preferably from 2000 g/mol to 300 000 g/mol. The ionic water-soluble block A has a molar mass ranging from 600 g/mol to 300 000 g/mol and preferably from 1200 g/mol to 180 000 g/mol. The hydrophobic block B has a molar mass ranging from 400 g/mol to 200 000 g/mol and preferably from 800 g/mol to 120 000 g/mol.

In order to have a water-soluble polymer, the proportion of the ionic hydrophilic block A in the polymer of the invention is greater than or equal to 50% by weight and is preferably greater than 60% by weight relative to the total weight of the triblock polymer (block A+blocks B).

According to one preferred embodiment of the invention, if the block polymer used in the composition of the invention contains an aromatic nucleus, this nucleus is present in only one block (A or B) but never simultaneously in blocks A and B.

According to one particular embodiment of the invention, the triblock polymer comprises, as block A, sodium polyacrylate and, as block B, polystyrene. It may be in particular polystyrene (2500 g/mol)—sodium polyacrylate (29 800 g/mol)—polystyrene (2500 g/mol).

The block polymers of the invention may be prepared by the synthetic processes conventionally used to obtain block polymers. Examples of preparation processes that may be mentioned include polymerizations of anionic or cationic type and controlled free-radical polymerization (see "New Method of Polymer Synthesis", Blackie Academic & Professional, London, 1995, Volume 2, page 1, or Trends Polym. Sci. 4, page 183 (1996) from C. J. Hawker), which may be carried out according to various processes such as, for example, the atom transfer approach (Atom Transfer Radical Polymerization or ATRP) (see JACS, 117, page 5614 (1995) from Matyjasezwski et al.), the method via radicals such as nitroxides (Georges et al., Macromolecules, 1993, 26, 2987) or the reversible chain transfer approach with addition-fragmentation (Radical Addition-Fragmentation chain Transfer) such as the MADIX process (Macromolecular Design via the Interchange of Xanthate) (Charmot D., Corpart P., Adam H., Zard S. Z., Biadatti T., Bouhadir G., Macromol. Symp., 2000, 150, 23). The triblock polymers used in the composition of the invention may be obtained by these synthetic processes. These processes may also be used to obtain only one of the two types of blocks of the polymer of the invention, the other block being introduced into the final polymer by means of the primer used or alternatively by a coupling reaction between the blocks A and B.

The amount of triblock polymer(s) in the composition of the invention can vary depending on the type of composition that it is desired to obtain and the desired degree of gelation. It can range, for example, from 0.01% to 20% by weight, preferably from 0.05% to 15% by weight and better still from 0.1% to 10% by weight relative to the total weight of the composition.

As above-mentioned, synergism is observed when the triblock polymers B-A-B are used with diblocks polymers A'-B comprising a neutral water-soluble polymer block A' and a hydrophobic polymer block B. Thus, the polymers of the invention may be used as gelling agents, either alone (one or more triblock polymers B-A-B) or in combination with one or more water-soluble or water-dispersible polymers of diblock structure A'-B in which A' is a neutral water-soluble polymer block and B is a hydrophobic polymer block as defined above for the triblock copolymer. The amount of ionic triblock polymer B-A-B in the mixture of ionic triblock polymers B-A-B and of neutral diblock polymers A'-B is greater than 10% by weight and preferably greater than 20% by weight relative to the total amount of triblock and diblock polymers, which means that, out of 100% of mixture, there must be at least 10% triblock polymer(s).

In the neutral water-soluble or water-dispersible polymers A'-B, the hydrophobic polymer block B has the same definition as that given above for the triblock polymers.

The neutral water-soluble block A' may be a polyoxyalkylenated and especially polyoxyethylenated or polyoxypropylenated polymer (homopolymer or copolymer) such as, for example, polyethylene oxide (PEO), polypropylene oxide (PPO), copolymers of ethylene oxide (EO) or of propylene oxide (PO) and mixtures thereof.

The neutral water-soluble block A' may also be obtained from one or more water-soluble monomers (If) and mixtures thereof, such as, for example:

(meth)acrylamide,
N-vinylacetamide and N-methyl-N-vinylacetamide,
N-vinylformamide and N-methyl-N-vinylformamide,
N-vinyllactams including a cyclic alkyl group containing from 4 to 9 carbon atoms, such as N-vinyl-pyrrolidone, N-butyrolactam and N-vinylcaprolactam,
vinyl alcohol of formula $CH_2=CHOH$,
maleic anhydride,
vinylamine,
water-soluble vinyl monomers of formula (VI) below:

in which:
$R_{40}$ is chosen from H, $-CH_3$, $-C_2H_5$ and $-C_3H_7$;
$X_5$ is chosen from:
alkyloxides of the type $-OR_{41}$ in which $R_{41}$ is a linear or branched, saturated or unsaturated hydrocarbon radical containing from 1 to 6 carbon atoms, optionally substituted with a halogen atom (iodine, bromine, chlorine or fluorine); a hydroxyl ($-OH$); carboxylic acid ($-COOH$), ether ($-O-$); primary amine ($-NH_2$); secondary amine ($-NHR_{42}$) : or tertiary amine ($-NR_{42}R_{43}$) group, the radicals $R_{42}$ and $R_{43}$ being, independently of each other, a linear or branched, saturated or unsaturated hydrocarbon radical containing 1 to 6 carbon atoms, with the proviso that the sum of the carbon atoms of $R_{41}+R_{42}+R_{43}$ does not exceed 6.

As examples of water-soluble vinyl monomers of formula (VI) including ester groups, mention may be made of glycidyl (meth)acrylate, hydroxyethyl methacrylate and ethylene glycol (meth)acrylate, diethylene glycol (meth)acrylate or polyalkylene glycol (meth)acrylates.

groups $-NH_2$, $-NHR_{44}$ and $-NR_{44}R_{45}$ in which $R_{44}$ and $R_{45}$ are, independently of each other, linear or branched, saturated or unsaturated hydrocarbon radicals containing 1 to 6 carbon atoms, with the proviso that the total number of carbon atoms of $R_{44}+R_{45}$ does not exceed 6, the said radicals $R_{44}$ and $R_{45}$ optionally being substituted with a halogen atom (iodine, bromine, chlorine or fluorine); a carboxylic acid ($-COOH$); hydroxyl ($-OH$); ether ($-O-$); primary amine ($-NH_2$); secondary amine ($-NHR_{46}$); or tertiary amine ($-NR_{46}R_{47}$) group, the radicals $R_{46}$ and $R_{47}$ being, independently of each other, a linear or branched, saturated or unsaturated hydrocarbon radical containing 1 to 6 carbon atoms, with the proviso that the sum of the carbon atoms of $R_{44}+R_{45}+R_{46}+R_{47}$ does not exceed 6.

An example of a water-soluble vinyl monomer of formula (VI) including amide groups that may be mentioned is N,N-dimethylacrylamide.

the substituents $R_{40}$ and $X_5$ being such that the monomer of formula (VI) is water-soluble;
and mixtures of these monomers (If).

Along with the monomers (If), the neutral water-soluble block A' may optionally also be obtained from hydrophobic monomers (Ig), the said hydrophobic monomers being present in an amount that is low enough relative to the monomers (If) for the block A' to be water-soluble.

Examples of hydrophobic monomers (Ig) that may be mentioned include:

- styrene and its derivatives such as 4-butyl-styrene, α-methylstyrene and vinyltoluene,
- vinyl acetate of formula CH₂═CH—OCOCH₃;
- vinyl ethers of formula CH₂═CHOR₄₈ in which R₄₈ is a linear or branched, saturated or unsaturated hydrocarbon radical containing from 1 to 6 carbon atoms;
- acrylonitrile,
- caprolactone,
- vinyl chloride and vinylidene chloride,
- unsaturated silicone monomers, such as methacryloxypropyltris(trimethylsiloxy)silane and silicone methacrylamides,
- the hydrophobic vinyl monomers of formula (VII) below:

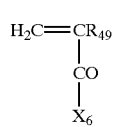

(VII)

in which:
  R₄₉ is chosen from H, —CH₃, —C₂H₅ and —C₃H₇;
  X₆ is chosen from:
    alkyloxides of the type —OR₅₀ in which R₅₀ is a linear or branched, saturated or unsaturated hydrocarbon radical containing from 1 to 6 carbon atoms. Examples of hydrophobic vinyl monomers of formula (VII) including ester groups that may be mentioned include methyl methacrylate, ethyl methacrylate, n-butyl (meth)acrylate, tert-butyl (meth)acrylate, cyclohexyl acrylate, isobornyl acrylate and 2-ethylhexyl acrylate;
    groups —NH₂, —NHR₅₁ and —NR₅₁R₅₂ in which R₅₁ and R₅₂ are, independently of each other, linear or branched, saturated or unsaturated hydrocarbon radicals containing 1 to 6 carbon atoms, with the proviso that the total number of carbon atoms of R₅₁+R₅₂ does not exceed 6;
  the substituents R₄₉ and X₆ being such that the monomer of formula (VII) is hydrophobic;
  and mixtures of these monomers (Ig).

The neutral diblock copolymers A'-B have a molar mass ranging from 1000 g/mol to 500 000 g/mol and preferably from 2000 g/mol to 300 000 g/mol. The neutral water-soluble block A' has a molar mass ranging from 500 g/mol to 250 000 g/mol and preferably from 1000 g/mol to 150 000 g/mol. The hydrophobic block B has a molar mass ranging from 500 g/mol to 250 000 g/mol and preferably from 1000 g/mol to 150 000 g/mol.

The amount of the neutral hydrophilic block A' in the diblock copolymer A'-B is greater than 50% of the total weight of the diblock polymer and preferably greater than 60% of the total weight of the diblock polymer.

The cosmetic or dermatological compositions of the invention may have a pH that varies within a wide range and that may be, for example, from 2 to 10, preferably from 3 to 8 and better still from 4 to 7.

The aqueous phase of the compositions according to the invention comprises at least water. The compositions of the invention may contain, in addition to water, at least one oily phase and/or one or more hydrophilic, lipophilic and/or amphiphilic organic solvents that are physiologically acceptable, i.e. well tolerated and that give a cosmetically acceptable feel.

The organic solvents can represent from 5% to 50% of the total weight of the composition. The organic solvents may be chosen from the group consisting of hydrophilic organic solvents, lipophilic organic solvents and amphiphilic solvents, or mixtures thereof. The amount of water preferably ranges from 10% to 99.99% by weight relative to the total weight of the composition.

Among the organic solvents that may be mentioned, for example, are linear or branched lower monoalcohols containing from 1 to 8 carbon atoms, for instance ethanol, propanol, butanol, isopropanol or isobutanol; polyols such as propylene glycol, isoprene glycol, butylene glycol, glycerol or sorbitol; monoalkyl or dialkyl isosorbide in which the alkyl groups contain from 1 to 5 carbon atoms, for instance dimethyl isosorbide; polyethylene glycols, especially those containing from 6 to 80 ethylene oxides; ethylene glycol ethers, for instance diethylene glycol monomethyl or monoethyl ether; propylene glycol ethers, for instance dipropylene glycol methyl ether; polyol esters and ethers, such as polypropylene glycol (PPG) esters and more especially fatty acid esters of polypropylene glycol (PPG), fatty alkyl ethers of PPG, for instance PPG-23 oleyl ether and PPG-36 oleate; fatty acid alkyl esters, such as diisopropyl adipate, dioctyl adipate or alkyl benzoates; and mixtures thereof.

The composition of the invention may comprise at least one fatty phase, also known as an oily phase. The fatty phase or oily phase may represent from 0% to 50% by weight relative to the total weight of the composition. In an emulsion, the oily phase preferably represents from 0.1% to 50% by weight and better still from 0.5% to 30% by weight relative to the total weight of the composition.

The fatty phase or oily phase usually contains at least one oil. As oils that may be used in the composition of the invention, mention may be made, for example, of:

- hydrocarbon-based oils of animal origin, such as perhydrosqualene;
- hydrocarbon-based oils of plant origin, such as liquid triglycerides of fatty acids containing from 4 to 10 carbon atoms, for instance heptanoic or octanoic acid triglycerides or alternatively, for example, sunflower oil, corn oil, soybean oil, marrow oil, grapeseed oil, sesame oil, hazelnut oil, apricot oil, macadamia oil, arara oil, sunflower oil, castor oil, avocado oil, caprylic/capric acid triglycerides, for instance those sold by the company Stearineries Dubois or those sold under the names Miglyol 810, 812 and 818 by the company Dynamit Nobel, jojoba oil or karite butter oil;
- synthetic esters and synthetic ethers, especially of fatty acids, for instance oils of formulae $R^{a}COOR^{b}$ and $R^{a}OR^{b}$ in which $R^{a}$ represents a fatty acid residue containing from 8 to 29 carbon atoms and $R^{b}$ represents a branched or unbranched hydrocarbon-based chain containing from 3 to 30 carbon atoms, such as, for example, purcellin oil, isononyl isononanoate, isopropyl myristate, 2-ethylhexyl palmitate, 2-octyl-dodecyl stearate, 2-octyldodecyl erucate or isostearyl isostearate; hydroxylated esters such as isostearyl lactate, octyl hydroxystearate, octyldodecyl hydroxystearate, diisostearyl malate, triisocetyl citrate and fatty alkyl heptanoates, octanoates and decanoates; polyol esters, for instance propylene glycol dioctanoate, neopentyl glycol diheptanoate and diethylene glycol diisononanoate; and pentaerythritol esters, for instance pentaerythrityl tetraisostearate;

linear or branched hydrocarbons of mineral or synthetic origin, such as volatile or non-volatile liquid paraffins, and derivatives thereof, petroleum jelly, polydecenes, and hydrogenated polyisobutene such as Parleam® oil;

fatty alcohols containing from 8 to 26 carbon atoms, for instance cetyl alcohol, stearyl alcohol and a mixture thereof (cetylstearyl alcohol), octyldodecanol, 2-butyloctanol, 2-hexyldecanol, 2-undecylpentadecanol, oleyl alcohol or linoleyl alcohol;

alkoxylated and especially ethoxylated fatty alcohols such as oleth-12, ceteareth-12 and ceteareth-20;

partially hydrocarbon-based and/or silicone-based fluoro oils, for instance those described in document JP-A-2 295 912. Examples of fluoro oils which may also be mentioned include perfluoromethylcyclopentane and perfluoro-1,3-dimethylcyclohexane, sold under the names "Flutec PC1®" and "Flutec PC3®" by the company BNFL Fluorochemicals; perfluoro-1,2-dimethylcyclobutane; perfluoroalkanes such as dodecafluoropentane and tetradecafluorohexane, sold under the names "PF 5050®" and "PF 5060 ®" by the company 3M, or alternatively bromoperfluorooctyl sold under the name "Foralkyl™" by the company Atochem; nonafluoromethoxybutane sold under the name "MSX 4518®" by the company 3M and nonafluoro-ethoxyisobutane; perfluoromorpholine derivatives, such as the 4-trifluoromethylperfluoromorpholine sold under the name "PF 5052®" by the company 3M;

silicone oils, for instance volatile or non-volatile polymethylsiloxanes (PDMSs) containing a linear or cyclic silicone chain, that are liquid or pasty at room temperature, especially cyclopolydimethylsiloxanes (cyclomethicones) such as cyclohexasiloxane; poly-dimethylsiloxanes comprising alkyl, alkoxy or phenyl groups, that are pendant or at the end of a silicone chain, these groups containing from 2 to 24 carbon atoms; phenylsilicones, for instance phenyltrimethicones, phenyldimethicones, phenyltrimethylsiloxydiphenylsiloxanes, diphenyldimethicones, diphenylmethyldiphenyltrisiloxanes, 2-phenylethyltrimethylsiloxysilicates and polymethylphenylsiloxanes;

mixtures thereof.

In the list of oils mentioned above, the expression "hydrocarbon-based oil" means any oil mainly comprising carbon and hydrogen atoms, and optionally ester, ether, fluoro, carboxylic acid and/or alcohol groups.

The other fatty substances that may be present in the oily phase are, for example, fatty acids containing from 8 to 30 carbon atoms, for instance stearic acid, lauric acid, palmitic acid and oleic acid; waxes, for instance lanolin, beeswax, carnauba wax or candelilla wax, paraffin waxes, lignite wax or microcrystalline waxes, ceresin or ozokerite, synthetic waxes such as polyethylene waxes, Fischer-Tropsch waxes; gums such as silicone gums (dimethiconol); silicone resins such as trifluoromethyl-C1-4-alkyl-dimethicone and trifluoropropyldimethicone; and silicone elastomers, for instance the products sold under the names "KSG" by the company Shin-Etsu, under the names "Trefil", "BY29" or "EPSX" by the company Dow Corning or under the names "Gransil" by the company Grant Industries.

These fatty substances may be chosen in a varied manner by a person skilled in the art so as to prepare a composition having the desired properties, for example in terms of consistency or texture.

The composition of the invention may comprise an aqueous phase alone, or an aqueous phase and a fatty phase (W/O or O/W emulsion) or several aqueous phases and one fatty phase (W/O/W emulsion) or one aqueous phase and several fatty phases (O/W/O emulsion). It may thus constitute a solution, a gel or an emulsion (simple or multiple).

When the composition is an emulsion, it may contain no emulsifying surfactant, but it may also contain at least one emulsifying surfactant. The emulsifying surfactants are chosen in a suitable manner according to the emulsion to be obtained (W/O or O/W emulsion).

For the O/W emulsions, it is possible to use, for example, as emulsifying surfactant, a nonionic emulsifying surfactant, for instance saccharide esters and ethers such as sucrose stearate, sucrose cocoate and the mixture of sorbitan stearate and of sucrose cocoate sold by the company ICI under the name Arlatone 2121®; polyol esters, in particular glycerol or sorbitol esters, such as glyceryl stearate, polyglyceryl-2 stearate and sorbitan stearate; glycerol ethers; oxyethylenated and/or oxypropylenated ethers such as the oxyethylenated, oxypropylenated ether of lauryl alcohol containing 25 oxyethylene groups and 25 oxypropylene groups (CTFA name "PPG-25 laureth-25") and the oxyethylenated ether of the mixture of $C_{12}$–$C_{15}$ fatty alcohols containing 7 oxyethylene groups (CTFA name "$C_{12}$–C15 Pareth-7") ; ethylene glycol polymers such as PEG-100, and mixtures thereof.

For the W/O emulsions, mention may be made, for example, as emulsifying surfactants, of fatty esters of a polyol, in particular of glycerol or of sorbitol, and in particular polyol isostearates, oleates and ricinoleates, such as the mixture of petrolatum, of polyglyceryl-3 oleate and of glyceryl isostearate, hydrogenated castor oil and of ozokerite, sold under the name Protegin W® by the company Goldschmidt, sorbitan isostearate, polyglyceryl diisostearate, polyglyceryl-2 sesquiisostearate; saccharide esters and ethers such as "methyl glucose dioleate"; fatty esters such as magnesium lanolate; dimethicone copolyols and alkyldimethicone copolyols such as Laurylmethicone copolyol sold under the name Dow Corning 5200 Formulation Aid by the company Dow Corning and Cetyl dimethicone copolyol sold under the name Abil EM 90® by the company Goldschmidt, and mixtures thereof.

The emulsifying surfactants may be introduced in unmodified form or in the form of a mixture with other emulsifying surfactants and/or with other compounds such as fatty alcohols or oils.

It is also possible to use, as emulsifiers, amphiphilic polymers such as modified acrylic copolymers such as, for example, the products sold under the names Pemulen by the company Goodrich; copolymers of 2-acrylamido-2-methylpropanesulfonic acid containing a hydrophobic chain, as described in document EP-A-1 069 142 incorporated here by way of reference; polyolefins containing an optionally esterified or amidated succinic end group, for instance the compounds described in documents U.S. Pat. Nos. 4,234,435, 4,708,753, 5,129,972, 4,931,110, GB-A-2 156 799 and U.S. Pat. No. 4,919,179, which are incorporated herein for reference. Polyolefins containing a succinic end group that may be mentioned especially include polyisobutylenes containing a modified succinic end group, such as the products sold under the names L2724 and L2721 by the company Lubrizol.

The amount of emulsifying surfactant can range from 0% to 1% in the emulsions said to be free of emulsifying surfactant. In the other emulsions, the amount of emulsifiers (emulsifying surfactant and/or amphiphilic polymer) can range from 0.01% to 10% of the total weight of the composition and preferably from 0.1% to 5% by weight relative to the total weight of the composition.

In a known manner, all the compositions of the invention can contain adjuvants that are common in cosmetics and dermatology, other standard hydrophilic or lipophilic thickeners and/or gelling agents; foaming surfactants; polymers; moisturizers; emollients; hydrophilic or lipophilic active agents; free-radical scavengers; sequestering agents; antioxidants; preserving agents; acidifying or basifying agents; fragrances; pigments; fillers; film-forming agents; dyestuffs and mixtures thereof. The amounts of these various adjuvants are those conventionally used in the fields under consideration.

Gelling Agents

Examples of gelling agents that may be mentioned include hydrophilic polymers such as carboxyvinyl polymers, for instance carbomers; 2-acrylamido-2-methylpropanesulfonic acid polymers that are soluble or dispersible in aqueous phase, for instance the polymer sold under the name "Hostacerin AMPS" by the company Clariant; synthetic neutral polymers, for instance polyvinylpyrrolidone (PVP) or polyvinyl acetate (PVA); polysaccharides, for instance guar gum, xanthan gum and cellulose derivatives such as, for example, hydroxyethylcellulose; water-soluble or water-dispersible silicone derivatives, for instance acrylic silicones and cationic silicones. Lipophilic gelling agents, such as modified clays or modified polysaccharides, may also be used.

Active Agents

As active agents that may be used in the composition of the invention, examples that may be mentioned include moisturizers and, for example, protein hydrolysates and polyols such as glycerol, glycols, for instance polyethylene glycols, and sugar derivatives; natural extracts; anti-inflammatory agents; procyannidol oligomers; vitamins, for instance vitamin A (retinol), vitamin C (ascorbic acid), vitamin E (tocopherol), vitamin B5 (panthenol), vitamin B3 (niacinamide), derivatives of these vitamins (especially esters) and mixtures thereof; urea; caffeine; depigmenting agents such as cojic acid, hydroquinone and caffeic acid; salicylic acid and its derivatives; α-hydroxy acids such as lactic acid and glycolic acid and derivatives thereof; retinoids such as carotenoids and vitamin A derivatives; sunscreens; hydrocortisone; melatonin; algal, fungal, plant, yeast or bacterial extracts; enzymes; DHEA and its derivatives and metabolites; antibacterial active agents, for instance 2,4,4'-trichloro-2'-hydroxydi-phenyl ether (or Triclosan), 3,4,4'-trichloro-carbanilide (or Triclocarban) and the acids indicated above and especially salicylic acid and its derivatives; matt-effect agents, for instance fibres; tensioning agents; and mixtures thereof.

Foaming Surfactants

Foaming surfactants that may be mentioned include nonionic, anionic, amphoteric and zwitterionic foaming surfactants and mixtures thereof.

The nonionic foaming surfactants may be chosen, for example, from alkyl polyglucosides (APG), maltose esters, polyglycerolated fatty alcohols, glucamine derivatives, for instance 2-ethylhexyl-oxycarbonyl-N-methylglucamine, and mixtures thereof. Alkylpolyglucosides that may be mentioned more particularly include decylglucoside (alkyl-C9/C11-polyglucoside (1.4)), for instance the product sold under the name Mydol 10® by the company Kao Chemicals, the product sold under the name Plantaren 2000 UP® by the company Henkel, and the product sold under the name Oramix NS 10® by the company SEPPIC; caprylyl/capryl glucoside, for instance the product sold under the name Oramix CG 110® by the company SEPPIC; lauryl glucoside, for instance the products sold under the names Plantaren 1200 N® and Plantacare 1200® by the company Henkel; and cocoglucoside, for instance the product sold under the name Plantacare 818/UP® by the company Henkel.

The anionic surfactants may be chosen especially from carboxylates; amino acid derivatives such as sarcosinates and especially acylsarcosinates, for instance sodium lauroyl sarcosinate or sodium myristoyl sarcosinate; alkyl sulfates; alkyl ether sulfates, for instance sodium lauryl ether sulfate and ammonium lauryl ether sulfate; sulfonates such as, for example, α-olefin sulfonates; isethionates and acylisethionates, for instance sodium cocoylisethionate; taurates; sulfosuccinates; alkyl sulfoacetates; phosphates and alkyl phosphates, for instance lauryl phosphate,; polypeptides; anionic derivatives of alkyl polyglucoside; fatty acid soaps, for instance the potassium or sodium salts of lauric, myristic, palmitic or stearic acid (potassium or sodium laurate, myristate, palmitate or stearate); and mixtures thereof.

The amphoteric and zwitterionic surfactants may be chosen, for example, from betaines, for instance cocobetaine, laurylbetaine, oxyethylenated laurylbetaine or oxyethylenated stearylbetaine; N-alkylamidobetaines, for instance cocamidopropyl betaine; glycine derivatives, for instance sodium or potassium N-cocoylglycinate; sultaines, for instance cocoyl-amidopropylhydroxysulfobetaine; alkyl poly-aminocarboxylates; alkylamphoacetates, for instance N-disodium N-cocoyl-N-carboxymethoxyethyl-N-carboxy-methylethylenediamine and N-sodium N-cocoyl-N-hydroxyethyl-N-carboxymethylethylenediamine; and mixtures thereof.

Sunscreens

The sunscreens may be chosen from organic screening agents and physical sunblock screening agents, and mixtures thereof.

Examples of UV-A-active and/or UV-B-active organic screening agents that may be mentioned include those designated above under their CTFA name:

Para-aminobenzoic Acid Derivatives:
 PABA,
 Ethyl PABA,
 Ethyl dihydroxypropyl PABA,
 Ethylhexyl dimethyl PABA sold in particular under the name "Escalol 507" by ISP,
 Glyceryl PABA,
 PEG-25 PABA sold under the name "Uvinul P25" by BASF,
Salicylic Derivatives:
 Homosalate sold under the name "Eusolex HMS" by Rona/EM Industries,
 Ethylhexyl salicylate sold under the name "Neo Heliopan OS" by Haarmann and Reimer,
 Dipropylene glycol salicylate sold under the name "Dipsal" by Scher,
 TEA salicylate sold under the name "Neo Heliopan TS" by Haarmann and Reimer,
Dibenzoylmethane Derivatives:
 Butyl methoxydibenzoylmethane sold in particular under the trade name "Parsol 1789" by Hoffmann La Roche,
 Isopropyldibenzoylmethane,
Cinnamic Derivatives:
 Ethylhexyl methoxycinnamate sold in particular under the name "Parsol MCX" by Hoffmann La Roche, Isoproyl methoxycinnamate,
Isoamyl methoxy cinnamate sold under the trade name "Neo Heliopan E 1000" by Haarmann and Reimer,
Cinoxate,
DEA methoxycinnamate,
Diisopropyl methylcinnamate,
Glyceryl ethylhexanoate dimethoxycinnamate
β,β'-diphenylacrylate Derivatives:
Octocrylene sold in particular under the trade name "Uvinul N539" by BASF,
Etocrylene, sold in particular under the trade name "Uvinul N35" by BASF,
Benzophenone Derivatives:
Benzophenone-1 sold under the trade name "Uvinul 400" by BASF,
Benzophenone-2 sold under the trade name "Uvinul D50" by BASF,
Benzophenone-3 or Oxybenzone, sold under the trade name "Uvinul M40" by BASF,
Benzophenone-4 sold under the trade name "Uvinul MS40" by BASF,
Benzophenone-5
Benzophenone-6 sold under the trade name "Helisorb 11" by Norquay
Benzophenone-8 sold under the trade name "Spectra-Sorb UV-24" by American Cyanamid
Benzophenone-9 sold under the trade name "Uvinul DS-49" by BASF,
Benzophenone-12
Benzylidenecamphor Derivatives:
3-Benzylidenecamphor manufactured under the name "Mexoryl SD" by Chimex,
4-Methylbenzylidene camphor sold under the name "Eusolex 6300" by Merck,
Benzylidenecamphorsulfonic acid manufactured under the name "Mexoryl SL" by Chimex,
Camphor benzalkonium methosulfate manufactured under the name "Mexoryl SO" by Chimex,
Terephthalylidenedicamphorsulfonic acid manufactured under the name "Mexoryl SX" by Chimex,
Polyacrylamidomethylbenzylidenecamphor manufactured under the name "Mexoryl SW" by Chimex,
Phenylbenzimidazole Derivatives:
Phenylbenzimidazolesulfonic acid sold in particular under the trade name "Eusolex 232" by Merck,
Benzimidazilate sold under the trade name "Neo Heliopan AP" by Haarmann and Reimer,
Triazine Derivatives:
Anisotriazine sold under the trade name "Tinosorb S" by Ciba-Geigy,
Ethylhexyltriazone sold in particular under the trade name "Uvinul T150" by BASF,
Diethylhexylbutamidotriazone sold under the trade name "Uvasorb HEB" by Sigma 3V,
Phenylbenzotriazole Derivatives:
Drometrizole trisiloxane sold under the name "Silatrizole" by Rhodia Chimie,
Anthranilic Derivatives:
Menthyl anthranilate sold under the trade name "Neo Heliopan MA" by Haarmann and Reimer,
Imidazoline Derivatives:
Ethylhexyldimethoxybenzylidenedioxoimidazoline propionate,
Benzylmalonate Derivatives:
Polyorganosiloxane containing benzalmalonate functions, sold under the trade name "Parsol SLX" by Hoffmann La Roche
and the mixtures thereof. ,
The organic UV screening agents that are more particularly preferred are chosen from the following compounds:
Ethylhexyl salicylate,
Butyl methoxydibenzoylmethane,
Ethylhexyl methoxycinnamate,
Octocrylene,
Phenylbenzimidazolesulfonic acid,
Terephthalylidenedicamphorsulfonic acid,
Benzophenone-3,
Benzophenone-4,
Benzophenone-5,
4-Methylbenzylidenecamphor,
Benzimidazilate,
Anisotriazine,
Ethylhexyltriazone,
Diethylhexylbutamidotriazone,
Methylenebis(benzotriazolyl)tetramethylbutylphenol
Drometrizole trisiloxane, and mixtures thereof.
Examples of physical sunblock screening agents that may be mentioned include titanium oxide or zinc oxide, in the form of optionally coated microparticles or nanoparticles (nanopigments), and mixtures thereof. Mention may be made, for example, of the hydrophilic nanotitanium sold under the name Mirasun TIW60 by the company Rhodia, and the lipophilic nanotitanium sold under the name MT100T by the company Tayca.

Pigments

Pigments are especially used in makeup compositions. Pigments that may be mentioned include mineral pigments and especially metal oxides such as titanium dioxide, zirconium dioxide or cerium dioxide, and also zinc oxide, iron oxide or chromium oxide, ferric blue, nacres such as mica coated with titanium oxide, with iron oxide, with natural pigment or with bismuth oxychloride, and also coloured titanium mica; and organic pigments such as carbon black and lakes, which are calcium, barium, aluminium or zirconium salts of acidic dyes such as halo acid dyes, azo dyes or anthraquinone dyes.

These pigments may be treated so as to make their surface hydrophobic; this treatment may be carried out according to methods known to those skilled in the art; the pigments may especially be coated with silicone compounds such as PDMSs and/or with polymers.

Fillers

Examples of fillers that may be mentioned, besides pigments, include silica powder; talc; polyamide particles and especially those sold under the name Orgasol by the company Atochem; polyethylene powders; microspheres based on acrylic copolymers, such as those made of ethylene glycol dimethacrylate/lauryl methacrylate copolymer, sold by the company Dow Corning under the name Polytrap; expanded powders such as hollow microspheres and especially the microspheres sold under the name Expancel by the company Kemanord Plast or under the name Micropearl F 80 ED by the company Matsumoto; powders of natural organic materials such as optionally crosslinked corn starch, wheat starch or rice starch, such as starch powders crosslinked with octenylsuccinic anhydride, sold under the name Dry-Flo by the company National Starch; silicone resin microbeads such as those sold under the name Tospearl by the company Toshiba Silicone; and mixtures thereof.

Needless to say, a person skilled in the art will take care to select the optional adjuvants added to the composition according to the invention such that the advantageous properties intrinsically associated with the composition in accordance with the invention are not, or are not substantially, adversely affected by the envisaged addition.

The compositions according to the invention may be in the form of gels, lotions, milks, more or less unctuous creams, or pastes. These compositions are prepared according to the usual methods. Since the block polymer used is water-soluble, it is generally introduced in an aqueous phase.

The compositions of the invention may be used as care, treatment, protective, cleansing, makeup-removing and/or makeup products for keratin materials (skin, hair, scalp, eyelashes, eyebrows, nails or mucous membranes) such as protective, treatment or care creams for the face, for the hands or for the body, protective or care body milks, and gels or mousses to care for the skin and/or mucous membranes (lips).

The compositions of the invention can contain sunscreens and can thus also be used as antisun products.

The compositions may be used for makeup, especially for making up the skin, the eyebrows, the eyelashes and the lips, such as face creams, foundations, mascaras or lipsticks. Such products generally contain pigments.

The compositions according to the invention may also be used as rinse-out products or as leave-in products for cleansing facial skin and/or body skin and/or for cleansing the hair, for example as haircare products, including haircare and hair conditioning products.

A subject of the invention is the cosmetic use of a cosmetic composition as defined above, as a rinse-out or leave-in hair product.

A subject of the invention is the cosmetic use of a cosmetic composition as defined above, as a product for cleansing and/or removing makeup from the skin and/or the eyes.

A subject of the invention is also the cosmetic use of a cosmetic composition as defined above, as a care product for the skin, the hair, the scalp, the eyelashes, the eyebrows, the nails or mucous membranes.

A subject of the invention is also the cosmetic use of a cosmetic composition as defined above, as a makeup product.

A subject of the invention is also the cosmetic use of a cosmetic composition as defined above, as an antisun product (for protection against sunlight and/or the UV radiation of tanning machines).

Another subject of the invention is a (non-therapeutic) cosmetic process for treating a keratin material such as the skin, the scalp, the hair, the eyelashes, the eyebrows, the nails or the mucous membranes, characterized in that a cosmetic composition as defined above is applied to the keratin material.

EXAMPLES

The gelling power of the polymers was demonstrated by rheology using a rheometer of RS150 type (Haake) operating under controlled stress, and equipped with a 35 mm/2° cone/plate geometry. A Peltier-effect temperature control system makes it possible to maintain the sample at a temperature of 20° C. during the measurements. The Theological characterizations were performed in flow and dynamic modes.

Flow Measurements:

The measurements are carried out by imposing an ascending stress ramp and a descending stress ramp at equilibrium from 0 Pa up to a stress corresponding to a shear rate of 500 $s^{-1}$. These measurements make it possible to evaluate the viscosity of the studied systems for shear rates equal to 0.001 $s^{-1}$, 0.01 $s^{-1}$ and 100 $s^{-1}$.

Dynamic Measurements:

The limits of the linear viscoelastic domains were determined at $10^{-2}$ and 1 Hz by subjecting the sample to a series of sinusoidal stresses of fixed frequency and of logarithmically distributed increasing amplitudes between two limits at a rate of 5 points per decade. The linear viscoelastic behaviour is then characterized by subjecting the sample to a series of 20 sinusoidal stresses of logarithmically distributed frequencies between 10 and $10^{-2}$ Hz and of amplitudes such that the deformation amplitude is constant and located in the linear domain previously determined. These measurements make it possible to evaluate the complex modulus G★ at 1 Hz and the loss angle δ at 1 Hz, in the linear viscoelastic domain. G★ and δ are the viscoelastic parameters used to measure the physical properties of viscoelastic fluids, as explained in "An introduction to rheology" by H. A. Barnes, J. F. Hutton and K. Walters, pages 46 to 54 (published by Elsevier 1989). The modulus G★ is equal to the square root of the sum of the squares of the elastic modulus G' (storage modulus) and the loss modulus G" (loss modulus). The tangent of the loss angle δ is equal to the ratio G"/G'.

In the following examples, the triblock polymer used was prepared by anionic polymerization.

Example 1

Aqueous solution containing 0.6% (by weight) of a polystyrene (2500 g/mol)—sodium polyacrylate (29 800 g/mol)—polystyrene (2500 g/mol) triblock polymer. In this block polymer, the amount of polymer block A represents 85.63% of the total weight of the triblock polymer.

This solution is prepared by simple dissolution of the adequate amount of polymer in the form of powder in demineralized water, with stirring at 25° C. The preparation of this solution does not require a specific dispersion process. This solution is transparent and gelled.

Flow Rheological Measurements:

Viscosity (0.001 $s^{-1}$)=2000 Pa.s

Viscosity (100 $s^{-1}$)=0.3 Pa.s

Dynamic Rheological Measurements:

G★ (1 Hz)=45 Pa

δ (1 Hz)=8°

The polystyrene (2500 g/mol)—sodium polyacrylate (29 800 g/mol)—polystyrene (2500 g/mol) triblock polymer has water-gelling power at a low mass concentration (0.6%). This solution has a pronounced shear-thinning nature and a pronounced elastic behaviour. The gelling power of this polymer is reproducible between different batches.

Example 2

Aqueous solution containing 3% (by weight) of a polystyrene (2500 g/mol)—sodium polyacrylate (29 800 g/mol)—polystyrene (2500 g/mol) triblock polymer. In this block polymer, the amount of polymer block A represents 85.63% of the total weight of the triblock polymer.

This solution is prepared by simple dissolution of the adequate amount of polymer in powder form into demineralized water, with stirring at 25° C. The preparation of this solution does not require a specific dispersion process. This solution is transparent and gelled.

Flow Rheological Measurements:

Viscosity $(0.001\ s^{-1})$=20 000 Pa.s

Viscosity $(100\ s^{-1})$=8 Pa.s

Dynamic Rheological Measurements:

G★ (1 Hz)=1200 Pa

δ (1 Hz)=4°

The polystyrene (2500 g/mol)—sodium polyacrylate (29 800 g/mol)—polystyrene (2500 g/mol) triblock polymer has a mass concentration equal to 3% and greater gelling power than at a concentration of 0.6%. Its elastic behaviour is also more pronounced. The gelling power of this polymer is reproducible between different batches.

Example 3

Aqueous solution comprising 2% (by weight) of a Polystyrene (2500 g/mole)—Sodium Polyacrylate (29 800 g/mole)—Polystyrene (2500 g/mole) triblock polymer. In this block polymer, the amount of polymer block A represents (water soluble block sodium polyacrylate) represents 85.63% of the total weight of the triblock polymer.

This solution is prepared by simple dissolution of the adequate amount of polymer in powder form into demineralized water, with stirring at 25° C. during 7 hours. A clear gel is obtained.

Rheological Measurement in Dynamic Mode:

These measurements have been performed using a Rheometrics RFS III rheometer equiped with a cone plate geometry 25 mm/0.04 rad, in the following conditions:

Strain=0.15% in order to verify the linear viscoelastic conditions,

Frequency ranging from 0.01 rad/s to 100 rad/s,

Values of the storage and loss moduli measured at a frequency of 1 rad/s are the following:

G' (1 rad/s)=350 Pa

G" (1 rad/s)=50 Pa

These results show that this triblock polymer presents good gelling properties for a 2% (by weight) polymer concentration.

Example 4

An aqueous solution of a mixture of triblock and diblock polymers is prepared. This aqueous solution contains 0.6% by weight of a polystyrene (2500 g/mol)—sodium polyacrylate (29 800 g/mol)—polystyrene (2500 g/mol) triblock polymer and 0.6% by weight of a polystyrene (3600 g/mol)-polyethylene oxide (7000 g/mol) diblock polymer.

This solution is prepared by dissolving the adequate amount of polymers in powder form into demineralized water, with stirring at 25° C. The solution obtained is transparent and gelled.

Flow Rheological Measurements:

Viscosity $(0.01\ s^{-1})$=3000 Pa.s

Viscosity $(100\ s^{-1})$=1 Pa.s

Dynamic Rheological Measurements:

G★ (1 Hz)=220 Pa

δ (1 Hz)=7°

Comparative Test

The gelling power obtained with the mixture of triblock and diblock polymers of Example 3 is compared with that obtained with the triblock polymer (Example 1) and that obtained with the diblock polymer alone. To evaluate the gelling power of the diblock polymer, an aqueous solution containing 0.6% by weight of the polystyrene (3600 g/mol)-polyethylene oxide (7000 g/mol) diblock polymer is prepared.

The solution is prepared by dissolving the adequate amount of polymer in powder form into demineralized water, with stirring at 25° C. The solution obtained is transparent and fluid.

Flow Rheological Measurements:

Viscosity $(0.01\ s^{-1})$=0.012 Pa.s

Viscosity $(100\ s^{-1})$=0.009 Pa.s

The polystyrene (3600 g/mol)-polyethylene oxide (7000 g/mol) diblock polymer is soluble in water at a concentration of 0.6% by weight, but it has no water-gelling power under these concentration conditions.

On the other hand, as shown by the rheological measurements of Example 3, the combination of the polystyrene (2500 g/mol)—sodium polyacrylate (29 800 g/mol)—polystyrene (2500 g/mol) triblock polymer and of the polystyrene (3600 g/mol)-polyethylene oxide (7000 g/mol) diblock polymer makes it possible to obtain a gelled aqueous solution with low mass concentrations (0.6% of each polymer).

Synergism is observed since the gelling properties observed for the combination are very much greater than those of solutions containing 0.6% of each of the diblock and triblock polymers considered separately (see Example 1 and above result). These results demonstrate a synergistic gelling effect for the mixture of the ionic triblock polymer B-A-B and the neutral diblock polymer A'-B.

Example 5

Effect of Surfactants on the Gelling Power

This example demonstrates the maintenance of the gelling power of the polymers used according to the invention, in the presence of surfactants.

An aqueous solution containing 1.2% (by weight) of a polystyrene (2500 g/mol)—sodium polyacrylate (29 800 g/mol)—polystyrene (2500 g/mol) triblock polymer is prepared by simple dissolution of the adequate amount of polymer in powder form into demineralized water, with stirring at 25° C. This solution is transparent and gelled.

Without Surfactant:

Flow Rheological Measurements:

Viscosity $(0.01\ s^{-1})$=500 Pa.s

Viscosity $(100\ s^{-1})$=1 Pa.s

With 0.24% nonionic surfactant (PEG-100 stearate):

Viscosity (0.01 s$^{-1}$)=500 Pa.s

Viscosity (100 s$^{-1}$)=1 Pa.s

With 1.2% nonionic surfactant (PEG-100 stearate):

Viscosity (0.01 s$^{-1}$)=40 Pa.s

Viscosity (100 s$^{-1}$)=0.4 Pa.s

Even though the gelling power has decreased slightly with this level of surfactant, it still exists.

Composition Examples

The examples below of emulsions according to the invention are given by way of illustration and with no limiting nature. The amounts therein are given as weight percentages, except where otherwise mentioned.

Example 6

Anti-ageing Serum

| | |
|---|---|
| Polystyrene (2500 g/mol) -sodium polyacrylate (29 800 g/mol) - polystyrene (2500 g/mol) triblock polymer | 0.6% |
| Preserving agent | 0.2% |
| Ascorbic acid | 10% |
| Dipropylene glycol | 5% |
| Demineralized water | 84.2% |

The serum is prepared by dissolving the triblock polymer in demineralized water containing the preserving agent, the ascorbic acid and the dipropylene glycol, with stirring for 2 hours.

The polystyrene (2500 g/mol)—sodium polyacrylate (29 800 g/mol)—polystyrene (2500 g/mol) triblock polymer by itself allows the aqueous phase to be thickened. The formulation obtained is an anti-ageing serum with an appealing texture.

Example 7

Body Milk (O/W Emulsion Without Emulsifying Surfactant)

| | |
|---|---|
| Aqueous phase: | |
| Polystyrene (2500 g/mol) -sodium polyacrylate (29 800 g/mol) - polystyrene (2500 g/mol) triblock polymer | 0.52% |
| Preserving agent | 0.2% |
| Demineralized water | 84.28% |
| Oily phase | |
| Parleam oil | 9% |
| Cyclohexadimethylsiloxane | 6% |

Procedure: The aqueous phase is prepared by dissolving the polymer in demineralized water containing the preserving agent, with stirring for 2 hours. The oily phase is then introduced slowly into the aqueous phase with stirring.

The polystyrene (2500 g/mol)—sodium polyacrylate (29 800 g/mol)—polystyrene (2500 g/mol) triblock polymer by itself allows the aqueous phase to be gelled and allows all of the oily phase to be emulsified. An attractive gelled emulsion that may be used as a body milk is obtained.

Example 8

Moisturizing Cream (O/W Emulsion Without Emulsifying Surfactant)

| | |
|---|---|
| Aqueous phase: | |
| Polystyrene (2500 g/mol) -sodium polyacrylate (29 800 g/mol)-polystyrene (2500 g/mol) triblock polymer | 2.6% |
| Preserving agent | 0.2% |
| Demineralized water | 82.2% |
| Oily phase: | |
| Parleam oil | 9% |
| Cyclohexadimethylsiloxane | 6% |

Procedure: The aqueous phase is prepared by dissolving the polymer in demineralized water containing the preserving agent, with stirring for 2 hours. The oily phase is then introduced slowly into the aqueous phase with stirring.

The polystyrene (2500 g/mol)—sodium polyacrylate (29 800 g/mol)—polystyrene (2500 g/mol) triblock polymer by itself allows the aqueous phase to be gelled and allows all of the oily phase to be emulsified. An attractive gelled emulsion that may be used as a moisturizing cream is obtained.

The invention claimed is:

1. A cosmetic, dermatological or cosmetic and dermatological composition comprising a physiologically acceptable medium and at least one aqueous phase, the aqueous phase comprising water and at least one water soluble or water-dispersible triblock polymer having an B-A-B structure in which A is an ionic water-soluble polymer block where in A is (meth)acrylic acid or salts there of and B is a hydrophobic polymer block where in B is styrene or its derivatives, wherein the amount of polymer block A is greater than or equal to 50% of the total weight of the triblock polymer.

2. A composition according to claim 1, wherein the ionic water-soluble block A further comprises polymerized units of one or more monomers selected from the group consisting of hydrophobic monomers (Ib), neutral water-soluble monomers (Ic), and mixtures thereof.

3. A composition according to claim 2, wherein the ionic water-soluble block A further comprises polymerized units of one or more hydrophobic monomers (Ib) selected from the group consisting of:

styrene and its derivatives;

vinyl acetate;

vinyl ethers of formula $CH_2=CHOR_{12}$ in which $R_{12}$ is a linear or branched, saturated or unsaturated hydrocarbon radical containing from 1 to 6 carbon atoms;

acrylonitrile;

caprolactone;

vinyl chloride and vinylidene chloride;

unsaturated silicone monomers;

hydrophobic vinyl monomers of formula (II) below:

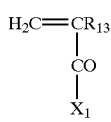

(II)

in which:
R$_{13}$ is selected from the group consisting of H, —CH$_3$, —C$_2$H$_5$ and —C$_3$H$_7$;
X$_1$ is selected from the group consisting of:
  alkyloxides of the formula —OR$_{14}$ in which R$_{14}$ is a linear or branched, saturated or unsaturated hydrocarbon radical containing from 1 to 6 carbon atoms;
  groups —NH$_2$, —NHR$_{15}$ and —NR$_{15}$R$_{16}$ in which R$_{15}$ and R$_{16}$ are, independently of each other, linear or branched, saturated or unsaturated hydrocarbon radicals containing 1 to 6 carbon atoms, with the proviso that the total number of carbon atoms of R$_{15}$+R$_{16}$ does not exceed 6;
the substituents R$_{13}$ and X$_1$ being such that the monomer of formula (II) is hydrophobic; and
mixtures of these monomers.

4. A composition according to claim 2, wherein the ionic water-soluble block A further comprises polymerized units of one or more neutral water-soluble monomers (Ic) selected from the group consisting of:
  (meth)acrylamide,
  N-vinylacetamide and N-methyl-N-vinylacetamide,
  N-vinylformamide and N-methyl-N-vinylformamide,
  maleic anhydride,
  vinylamine,
  N-vinyllactams including a cyclic alkyl group containing from 4 to 9 carbon atoms,
  vinyl alcohol,
  water-soluble vinyl monomers of formula (III) below:

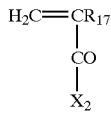

(III)

in which:
R$_{17}$ is selected from the group consisting of H, —CH$_3$, —C$_2$H$_5$ and —C$_3$H$_7$
X$_2$ is selected from the group consisting of:
  alkyloxides of the formula —OR$_{18}$ in which R$_{18}$ is a linear or branched, saturated or unsaturated hydrocarbon radical containing from 1 to 6 carbon atoms, optionally substituted with a halogen atom; a hydroxyl; carboxylic acid; ether; primary amine; secondary amine of the formula-NHR$_{19}$ or tertiary amine of the formula-NR$_{19}$R$_{20}$; the radicals R$_{19}$ and R$_{20}$ being, independently of each other, a linear or branched, saturated or unsaturated hydrocarbon radical containing 1 to 6 carbon atoms, with the proviso that the sum of the carbon atoms of R$_{18}$+R$_{19}$+R$_{20}$ does not exceed 6;
  groups —NH$_2$, —NHR$_{21}$ and —NR$_{21}$R$_{22}$ in which R$_{21}$ and R$_{22}$ are, independently of each other, linear or branched, saturated or unsaturated hydrocarbon radicals containing 1 to 6 carbon atoms, with the proviso that the total number of carbon atoms of R$_{21}$+R$_{22}$ does not exceed 6, the said radicals R$_{21}$ and R$_{22}$ optionally being substituted with a halogen atom; a carboxylic acid; hydroxyl; ether; primary amine; secondary amine of the formula-NHR$_{23}$; or tertiary amine of the formula-NR$_{23}$R$_{24}$, the radicals R$_{23}$ and R$_{24}$ being, independently of each other, a linear or branched, saturated or unsaturated hydrocarbon radical containing 1 to 6 carbon atoms, with the proviso that the sum of the carbon atoms of R$_{21}$+R$_{22}$+R$_{23}$+R$_{24}$ does not exceed 6;
the substituents R$_{17}$ and X$_2$ being such that the monomer of formula (III) is water-soluble; and
mixtures of these monomers.

5. A composition according to claim 1, wherein the ionic water-soluble block A is totally or partially neutralized with a mineral or organic base.

6. A composition according to claim 1, wherein the hydrophobic block B further comprises polymerized units of one or more ionic or neutral water soluble monomers (Ie) selected from the group consisting of the following monomers, or salts thereof:
  (meth)acrylic acid;
  styrenesulfonic acid;
  vinylsulfonic acid and (meth)allylsulfonic acid;
  vinylphosphonic acid;
  maleic anhydride;
  maleic acid;
  itaconic acid;
  crotonic acid;
  dimethyldiallylammonium chloride;
  methylvinylimidazolium chloride;
  (meth)acrylamide;
  N-vinylacetamide and N-methyl-N-vinylacetamide;
  N-vinylformamide and N-methyl-N-vinylformamide;
  N-vinyllactams including a cyclic alkyl group containing from 4 to 9 carbon atoms;
  vinyl alcohol;
  2-vinylpyridine and 4-vinylpyridine;
  the water-soluble vinyl monomers of formula (V) below:

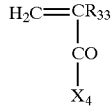

(V)

in which:
R$_{33}$ is selected from the group consisting of H, —CH$_3$, —C$_2$H$_5$ and —C$_3$H$_7$;
X$_4$ is selected from the group consisting of:
  alkyloxides of the formula —OR$_{34}$ in which R$_{34}$ is a linear or branched, saturated or unsaturated hydrocarbon radical containing from 1 to 6 carbon atoms, optionally substituted with a halogen atom; a carboxylate, carboxylic acid, sulfonic, sulfate, phosphate, hydroxyl, ether, primary amine, secondary amine of the formula-NHR$_{35}$, tertiary amine of the formula-NR$_{35}$R$_{36}$, or quaternary ammonium group of the formula-N$^+$R$_{35}$R$_{36}$R$_{37}$, the radicals R$_{35}$, R$_{36}$ and R$_{31}$ being, independently of each other, a linear or branched, saturated or unsaturated hydrocarbon radical containing 1 to 6 carbon atoms, with the proviso that the sum of the carbon atoms of R$_{34}$+R$_{35}$+R$_{36}$+R$_{37}$ does not exceed 6;

groups —NH$_2$, —NHR$_{38}$ and —NR$_{38}$R$_{39}$ in which the radicals R$_{38}$ and R$_{39}$ are, independently of each other, linear or branched, saturated or unsaturated hydrocarbon radicals containing 1 to 6 carbon atoms, with the proviso that the total number of carbon atoms of R$_{38}$+R$_{39}$ does not exceed 6, the said radicals R$_{38}$ and/or R$_{39}$ optionally being substituted with a halogen atom; a carboxylate; carboxylic acid; sulfonic; sulfate; phosphate; hydroxyl; ether; primary amine; secondary amine of the formula-NHR$_{35}$; tertiary amine of the formula-NR$_{35}$R$_{36}$ or quaternary ammonium group of the formula-N$^+$R$_{35}$R$_{36}$R$_{37}$, in which R$_{35}$, R$_{36}$ and R$_{37}$ have the same meaning as mentioned above, with the proviso that the sum of the carbon atoms of R$_{38}$+R$_{39}$+R$_{35}$+R$_{36}$+R$_{37}$ does not exceed 6;

the substituents R$_{33}$ and X$_4$ being such that the monomer of formula (V) is water-soluble; and mixtures of these monomers.

7. A composition according to claim 1, wherein the triblock polymer has a molar weight ranging from 1000 g/mol to 500 000 g/mol.

8. A composition according to claim 7, wherein the triblock polymer has a molar mass ranging from 2000 g/mol to 300 000 g/mol.

9. A composition according to claim 1, wherein the proportion of the ionic hydrophilic block A in the copolymer is greater than 60% by weight relative to the total weight of the blocks A and B.

10. A composition according to claim 1, wherein the amount of polymer ranges from 0.01% to 20% by weight relative to the total weight of the composition.

11. A composition according to claim 1, further comprising at least one water-soluble or water-dispersible diblock polymer A'-B in which A' is a neutral water-soluble polymer block and B is a hydrophobic polymer block.

12. A composition according to claim 11, wherein the block A' comprises polymerized units of one or more water-soluble monomers selected from the group consisting of the monomers (If) below:

(meth)acrylamide,

N-vinylacetamide and N-methyl-N-vinylacetamide,

N-vinylformamide and N-methyl-N-vinylformamide,

N-vinyllactams including a cyclic alkyl group containing from 4 to 9 carbon atoms, vinyl alcohol, maleic anhydride, vinylamine, water-soluble vinyl monomers of formula (VI) below:

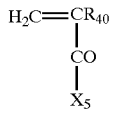

(VI)

in which:

R$_{40}$ is selected from the group consisting of H, —CH$_3$, —C$_2$H$_5$ and —C$_3$H$_7$;

X$_5$ is selected from the group consisting of:

alkyloxides of the formula —OR$_{41}$ in which R$_{41}$ is a linear or branched, saturated or unsaturated hydrocarbon radical containing from 1 to 6 carbon atoms, optionally substituted with a halogen atom; a carboxylic acid; hydroxyl; ether; primary amine; secondary amine of the formula-NHR$_{42}$; or tertiary amine of the formula-NR$_{42}$R$_4$; the radicals R$_{42}$ and R$_{43}$ being, independently of each other, a linear or branched, saturated or unsaturated hydrocarbon radical containing 1 to 6 carbon atoms, with the proviso that the sum of the carbon atoms of R$_{41}$+R$_{42}$+R$_{43}$ does not exceed 6;

groups —NH$_2$, —NHR$_{44}$ and —NR$_{44}$R$_{45}$ in which R$_{44}$ and R$_{45}$ are, independently of each other, linear or branched, saturated or unsaturated hydrocarbon radicals containing 1 to 6 carbon atoms, with the proviso that the total number of carbon atoms of R$_{44}$+R$_{45}$ does not exceed 6, the said radicals R$_{44}$ and R$_{45}$ optionally being substituted with a halogen atom; a carboxylic acid; hydroxyl; ether; primary amine; secondary amine of the formula-NHR$_{46}$; or tertiary amine of the formula-NR$_{46}$R$_{47}$, the radicals R$_{46}$ and R$_{47}$ being, independently of each other, a linear or branched, saturated or unsaturated hydrocarbon radical containing 1 to 6 carbon atoms, with the proviso that the sum of the carbon atoms of R$_{44}$+R$_{45}$+R$_{46}$ and R$_{47}$ does not exceed 6;

the substituents R$_{40}$ and X$_5$ being such that the monomer of formula (VI) is water-soluble; and mixtures of these monomers.

13. A composition according to claim 12, wherein the neutral water-soluble block A' further comprises polymerized units of one or more hydrophobic monomers (Ig) selected from the group consisting of the following monomers:

styrene and its derivatives, vinyl acetate, vinyl ethers of formula CH$_2$=CHOR$_{48}$ in which R$_{48}$ is a linear or branched, saturated or unsaturated hydrocarbon radical containing from 1 to 6 carbon atoms, acrylonitrile, caprolactone, vinyl chloride and vinylidene chloride, unsaturated silicone monomers, the hydrophobic vinyl monomers of formula (VII) below:

(VII)

in which:

R$_{49}$ is selected from the group consisting of H, —CH$_3$, —C$_2$H$_5$ and —C$_3$H$_7$;

X$_6$ is selected from the group consisting of:

alkyloxides of the formula —OR$_{50}$ in which R$_{50}$ is a linear or branched, saturated or unsaturated hydrocarbon radical containing from 1 to 6 carbon atoms;

groups —NH$_2$, —NHR$_{51}$ and —NR$_{51}$R$_{52}$ in which R$_{51}$ and R$_{52}$ are, independently of each other, linear or branched, saturated or unsaturated hydrocarbon radicals containing 1 to 6 carbon atoms, with the proviso that the total number of carbon atoms of R$_{51}$+R$_{52}$ does not exceed 6;

the substituents R$_{49}$ and X$_6$ such that the monomer of formula (VII) is hydrophobic; and mixtures thereof.

14. A composition according to claim 11, wherein the neutral diblock polymer has a molar mass ranging from 1000 g/mol to 500 000 g/mol.

15. A composition according to claim 11, wherein the amount of neutral hydrophilic block A' in the diblock polymer A'-B is greater than 50% of the total weight of the diblock polymer.

16. A composition according to claim 1, further comprising a physiologically acceptable medium.

17. A composition according to claim 1, further comprising at least one organic solvent selected from the group consisting of hydrophilic organic solvents, lipophilic organic solvents, amphiphilic solvents, and mixtures thereof.

18. A composition according to claim 17, comprising an organic solvent selected from the group consisting of monoalcohols containing from 1 to 8 carbon atoms, polyols, monoalkyl and dialkyl isosorbides, polyethylene glycols, ethylene glycol ethers, propylene glycol ethers, polyol ethers, polyol esters, fatty acid alkyl esters, and mixtures thereof.

19. A composition according to claim 17, wherein the organic solvent represents from 5% to 50% of the total weight of the composition.

20. A composition according to claim 1, in the form of a solution, a gel or an emulsion.

21. A composition according to claim 1, further comprising at least one oily phase.

22. A composition according to claim 21, wherein the oily phase comprises at least one oil.

23. A composition according to claim 1, in the form of an O/W, W/O, W/O/W or O/W/O emulsion.

24. A composition according to claim 1, further comprising at least one adjuvant selected from the group consisting of gelling agents and/or thickeners; polymers; foaming surfactants; moisturizers; emollients; hydrophilic or lipophilic active agents; free-radical scavengers; sequestering agents; antioxidants; preserving agents; acidifying or basifying agents; fragrances; pigments; fillers; filmforming agents; dyestuffs; and mixtures thereof.

25. A composition according to claim 24, comprising an active agent selected from the group consisting of protein hydrolysates; anti-inflammatory agents; polyols; sugar derivatives; natural extracts; procyannidol oligomers; vitamins; urea; caffeine; depigmenting agents; salicylic acid and its derivatives; α-hydroxy acids; retinoids; sunscreens; hydrocortisone; melatonin; algal, fungal, plant, yeast or bacterial extracts; enzymes; DHEA and its derivatives and metabolites; antibacterial active agents; matt-effect agents; tensioning agents; and mixtures thereof.

26. A composition according to claim 25, comprising an active agent selected from the group consisting of vitamin A, vitamin C, vitamin E, vitamin B5, vitamin B3, derivatives thereof and mixtures thereof.

27. A composition according to claim 1, further comprising an active agent selected from the group consisting of Triclosan, Triclocarban, salicylic acid and its derivatives, and mixtures thereof.

28. A composition according to claim 1, further comprising a sunscreen selected from the group consisting of organic screening agents, physical sunblock screening agents, and mixtures thereof.

29. A composition according to claim 28, comprising an organic screening agent selected from the group consisting of para-aminobenzoic acid derivatives; salicylic derivatives; dibenzoylmethane derivatives; cinnamic derivatives; (β,β'-diphenylacrylate derivatives; benzophenone derivatives; benzylidenecamphor derivatives; phenylbenzimidazole derivatives; triazine derivatives; phenylbenzotriazole derivatives; anthranilic derivatives; imidazoline derivatives; benzalmalonate derivatives; and mixtures thereof.

30. A composition according to claim 1, further comprising a physical sunblock screening agent selected from the group consisting of titanium oxides, zinc oxides, and mixtures thereof.

31. A composition according to claim 1, further comprising a foaming surfactant selected from the group consisting of nonionic, anionic, amphoteric and zwitterionic surfactants, and mixtures thereof.

32. A composition according to claim 31, comprising a foaming surfactant selected from the group consisting of alkyl polyglucosides; maltose esters; polyglycerolated fatty alcohols; glucamine derivatives; carboxylates; amino acid derivatives; alkyl sulfates; alkyl ether sulfates; sulfonates; isethionates and acylisethionates; taurates; sulfosuccinates; alkyl sulfoacetates; phosphates and alkyl phosphates; polypeptides; anionic derivatives of alkyl polyglucoside; fatty acid soaps; betaines; N-alkylamidobetaines; glycine derivatives; sultaines; alkyl polyaminocarboxylates; alkyl amphoacetates; and mixtures thereof.

33. A composition according to claim 1, wherein said composition is in the form of an oil-in-water emulsion comprising an oily phase dispersed in an aqueous phase, and wherein the composition comprises from 0 to about 1% by weight of emulsifying surfactant relative to the total weight of the composition.

34. A composition according to claim 1, in the form of a care, treatment, protective, cleansing, makeup removing and/or makeup product for keratin materials.

35. A composition according to claim 34, wherein the keratin material is the skin.

36. A method for treating or caring for the skin, hair, scalp, eyelashes, eyebrows, nails or mucous membranes, comprising applying the composition of claim 1 thereto.

37. A method for treating or caring for the skin, hair, scalp, eyelashes, eyebrows, nails or mucous membranes, comprising applying the composition of claim 11 thereto.

38. The composition of claim 1, in the form of a rinse-out or leave-in hair product.

39. A method for cleansing and/or removing makeup from the skin and/or the eyes, comprising applying the composition of claim 1 to the skin and/or the eyes.

40. A method for cleansing and/or removing makeup from the skin and/or the eyes, comprising applying the composition of claim 11 to the skin and/or the eyes.

41. The composition of claim 1, further comprising at least one cosmetically or dermatologically acceptable adjuvant selected from the group consisting of an oils, thickeners, gelling agents, moisturizers, emollients, active agents, free-radical scavengers, sequestering agents, antioxidants, preservatives, fragrances, pigments, fillers, film-forming agents, dyestuffs, sunscreens and mixtures thereof.

42. The composition of claim 41, further comprising at least one cosmetically or dermatologically acceptable adjuvant selected from the group consisting of an oils, thickeners, gelling agents, moisturizers, emollients, active agents, free-radical scavengers, sequestering agents, antioxidants, preservatives, fragrances, pigments, fillers, film-forming agents, dyestuffs, sunscreens and mixtures thereof.

* * * * *